United States Patent [19]

Moser

[11] Patent Number: 5,274,157

[45] Date of Patent: Dec. 28, 1993

[54] PROTECTED FORMYLPENTANEDIOLS, HYDROXYMETHYLPENTANEDIOLS, PROCESS FOR THEIR PREPARATION AND INTERMEDIATES

[75] Inventor: Heinz Moser, Möhlin, Switzerland

[73] Assignee: Ciba-Geigy Corporation, Ardsley, N.Y.

[21] Appl. No.: 969,632

[22] Filed: Oct. 30, 1992

[30] Foreign Application Priority Data

Nov. 12, 1991 [CH] Switzerland ............... 3291/91

[51] Int. Cl.[5] ................ C07F 7/18; C07D 321/00; C07D 319/00
[52] U.S. Cl. ................. 556/464; 549/349; 549/350; 549/360; 549/363
[58] Field of Search .............. 556/464; 549/349, 350, 549/360, 363

[56] References Cited

FOREIGN PATENT DOCUMENTS

| | | |
|---|---|---|
| 266099 | 5/1888 | European Pat. Off. |
| 249859 | 12/1987 | European Pat. Off. |
| 8707300 | 12/1987 | PCT Int'l Appl. |
| 89081469 | 9/1989 | PCT Int'l Appl. |
| 9106556 | 5/1991 | PCT Int'l Appl. |

OTHER PUBLICATIONS

Synthesis; No. 9; Sep. 1985; pp. 817-845.
Tet. Lett.; vol. 27; No. 6; 1986, pp. 747-748.
J. Med Chem., vol. 32; pp. 1861-1865 (1989).
J. Med Chem. vol. 33; pp. 1353-1360 (1990).
Nucleosides & Nucleotides, 6 (182), pp. 233-237 1987.
Tetrahedron Letters, vol. 31, No. 10 pp. 1463-1466 (1990).
J. Chem. Soc. Chem. Commun pp. 1083-1084 (1987).
J. Org. Chem. vol. 54, 5268-5272, Inoue et al., 1989.
Tetrahedron Letters, vol. 27, No. 6, pp. 747-748 (1986) Ravenscroft, P. et al.
Synthesis, No. 9, 1985, pp. 817-845, Lalonde, M. et al.

*Primary Examiner*—Marianne M. Cintins
*Assistant Examiner*—Michael B. Hydorn
*Attorney, Agent, or Firm*—Kevin T. Mansfield; George R. Dohmann

[57] ABSTRACT

Compounds of the formula Ib

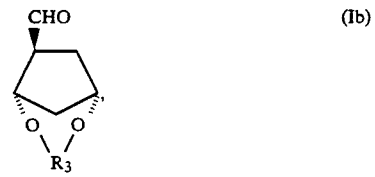

in which $R_1$ and $R_2$ independently of one another are linear or branched $C_1$-$C_{12}$alkyl, cycloalkyl having 5 to 8 ring carbon atoms, phenylalkyl having 1 to 4 C atoms in the alkylene group, the cyclic radicals being unsubstituted or substituted by $C_1$-$C_4$alkyl or $C_1$-$C_4$alkoxy, or $R_1$ and $R_2$ independently of one another are —$SiR_4R_5R_6$ in which $R_4$, $R_5$ and $R_6$ independently of one another are $C_1$-$C_{12}$alkyl, phenyl, benzyl, or phenyl or benzyl, each of which is substituted by $C_1$-$C_4$alkyl or $C_1$-$C_4$alkoxy, and $R_3$ is a bridging member which, together with the radical —OCH—$CH_2$—CHO— to which it is bonded, forms a 6- to 8-membered ring. These compounds are valuable intermediates for the preparation of carbacyclic nucleosides of the natural and unnatural series and of the racemates.

18 Claims, No Drawings

PROTECTED FORMYLPENTANEDIOLS, HYDROXYMETHYLPENTANEDIOLS, PROCESS FOR THEIR PREPARATION AND INTERMEDIATES

The invention relates to protected 4-formyl-1,3-pentanediols, protected 4-hydroxymethyl-1,3-pentanediols, to a process for their preparation, and to protected pent-4-ene-1,3-diols used as intermediates in the preparation process.

Carbacyclic nucleoside analogues have gained interest due to their antiviral properties and as units for oligonucleotides having antisense properties, see, for example, M. Bodenteich et al., Nucleosides & Nucleotides, 6(182), pages 233–237 1987, A. Szemzo et al., Tetrahedron Letters. Vol. 31, No. 10, pages 1463–1466 (1990), K. Biggadike et al., J. Chem. Soc., Chem. Commun., pages 1083–1084 (1987), J. Balzarini et al., J. Med. Chem., Vol. 32, pages 1861–1865 (1989), J. Beres et al., J. Med. Chem., Vol. 33, pages 1353–1360 (1990) and V. E. Marquez et al., Med. Res. Rev., Vol. 6, pages 1–40 (1986). The known methods for synthesis are highly complicated multistep processes in which the desired nucleoside analogues are only obtained in low yields. No satisfactory process has been found for the synthesis of the carbacyclic nucleoside analogues, both racemic and enantiomerically pure, in high yields. A process for the simultaneous preparation of such nucleoside analogues of the natural and unnatural series is also not known.

It has now been found that such nucleoside analogues can be prepared in high yields and high purity, both in the racemic and in enantioselective form, when protected 4-formyl-1,3-pentanediols are selected as starting compounds, it being possible to prepare nucleoside analogues of the natural and unnatural series simultaneously.

The present invention relates to compounds of the formulae Ia and Ib

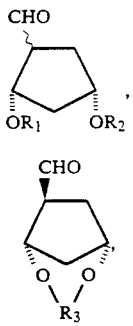

in which $R_1$ and $R_2$ independently of one another are linear or branched $C_1$–$C_{12}$alkyl, cycloalkyl having 5 to 8 ring carbon atoms, phenylalkyl having 1 to 4 C atoms in the alkylene group, the cyclic radicals being unsubstituted or substituted by $C_1$–$C_4$alkyl or $C_1$–$C_4$alkoxy, or $R_1$ and $R_2$ independently of one another are —SiR$_4$R$_5$R$_6$ in which R$_4$, R$_5$ and R$_6$ independently of one another are $C_1$–$C_{12}$alkyl, phenyl, benzyl, or phenyl or benzyl, each of which is substituted by $C_1$–$C_4$alkyl or $C_1$–$C_4$alkoxy, and R$_3$ is a bridging member which, together with the radical —OCH—CH$_2$—CHO— to which it is bonded, forms a 6- to 8-membered ring.

R$_1$ and R$_2$ are preferably identical radicals. R$_1$ and R$_2$, as alkyl, are preferably linear or branched $C_1$–$C_8$alkyl, particularly preferably $C_1$–$C_4$alkyl. Examples of alkyl are methyl, ethyl, and the isomers of propyl, butyl, pentyl, hexyl, heptyl, octyl, nonyl, decyl, undecyl and dodecyl. Preferred examples are methyl, ethyl, n- and i-propyl, n-, i- and t-butyl.

R$_1$ and R$_2$, as cycloalkyl, contain preferably 5 or 6 ring carbon atoms. Some examples of R$_1$ and R$_2$ as substituted or unsubstituted cycloalkyl are cyclopentyl, cyclohexyl, cyclooctyl, methylcyclopentyl, methylcyclohexyl and methoxycyclohexyl.

R$_1$ and R$_2$ as phenylalkyl are preferably substituted or unsubstituted phenylethyl, particularly preferably benzyl. Some preferred examples are benzyl, methylbenzyl, dimethylbenzyl and alkoxybenzyl.

In a preferred embodiment, R$_1$ and R$_2$ are identical radicals —SiR$_4$R$_5$R$_6$. R$_4$, R$_5$ and R$_6$ are preferably independently of one another $C_1$–$C_{12}$alkyl or phenyl. Particularly preferred are R$_4$, R$_5$ and R$_6$ $C_1$–$C_6$alkyl. Examples of alkyl have been mentioned above. Preferred examples of radicals —SiR$_4$R$_5$R$_6$ are trimethylsilyl, triethylsilyl, tri-n-propylsilyl, tri-i-propylsilyl, tri-n-butylsilyl, triphenylsilyl, t-butyldiphenylsilyl, phenyldimethylsilyl, i-propyldimethylsilyl, t- or n-butyldimethylsilyl, n-hexyldimethylsilyl, n-octyldimethylsilyl, n-dodecyldimethylsilyl and (1,1,2,2-tetramethylethyl)-dimethylsilyl.

Suitable bridging members for R$_3$ are, for example, alkylidene having 1 to 20 C atoms, cycloalkylidene having 5 to 8 ring carbon atoms, and radicals of the formulae R$_7$R$_8$Si= and —SiR$_7$R$_8$—O—R$_7$R$_8$Si— in which R$_7$ and R$_8$ independently of one another are linear or branched $C_1$–$C_{12}$alkyl, phenyl, benzyl, or phenyl or benzyl, each of which are substituted by $C_1$–$C_4$alkyl or $C_1$–$C_4$alkoxy.

R$_3$ as alkylidene contains preferably 1 to 14 C atoms. Examples of alkylidene are methylene, phenylmethylene, diphenylmethylene, phenyl-methyl-methylene, ethylidene, 1,1- or 2,2-propylidene, 1,1- or 2,2-butylidene, 1,1-, 2,2- or 3,3-pentylidene, 3,3-dimethyl-2,2-butylidene, 1,1-, 2,2- and 3,3-hexylidene, octylidene and dodecylidene. R$_3$ as alkylidene is particularly preferably $C_1$–$C_6$alkylidene and benzylidene. R$_3$ as cycloalkylidene is preferably cyclopentylidene and cyclohexylidene.

R$_7$ and R$_8$ in the radical R$_7$R$_8$Si= and in the radical —SiR$_7$R$_8$—O—R$_7$R$_8$Si— are preferably independently of one another $C_1$–$C_{12}$alkyl or phenyl, and particularly preferably $C_1$–$C_6$alkyl or phenyl. R$_7$ and R$_8$ are particularly preferably identical radicals. Examples of alkyl have been mentioned above. Preferred examples of these radicals are dimethylsilylidene, diethylsilylidene, di-n-propylsilylidene, di-i-propylsilylidene, di-n-butylsilylidene, di-i-butylsilylidene, di-t-butylsilylidene, diphenylsilylidene, phenylmethylsilylidene, i-propylmethylsilylidene, t- or n-butylmethylsilylidene, n-hexylmethylsilylidene, n-octylmethylsilylidene, n-dodecylmethylsilylidene and (1,1,2,2-tetramethylethyl)methylsilylidene and tetramethyl-, tetraethyl, tetra-n- or -i-propyl-, tetra-n- or tetra-i- or tetra-t-butyl-, 1,3-dimethyl-1,3-di-t-butyl-2-oxa-1,3-disila-prop-1,3-diyl.

A particularly preferred embodiment are the compounds of the formula Ib, in particular those in which R$_3$ is a radical R$_7$R$_8$Si= or a radical —SiR$_7$R$_8$—O—R$_7$R$_8$Si— in which R$_7$ and R$_8$ are preferably identical radicals and $C_1$–$C_6$alkyl.

The invention furthermore relates to a process for the preparation of the compounds of the formulae Ia and Ib which comprises a) reacting, in a first step, 1 equivalent of cis-1,3-pent-4-enediol, of the formula

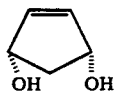

a1) with 2 equivalents of $R_1X$, $R_2X$ or mixtures of these, or a2) with one equivalent of $XR_3X$, in which $R_1$, $R_2$ and $R_3$ are as defined above and X or two X together are a leaving group, and b) hydroformylating the resulting compounds of the formulae IIa and IIb

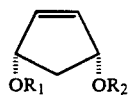 (IIa)

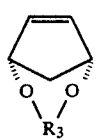 (IIb)

in a second step in the presence of a catalyst at increased temperature and under pressure with a mixture of $H_2$ and CO to give compounds of the formulae Ia and Ib.

The compounds of the formula IIb are novel and a further object of the invention. The abovementioned preferred meanings and enumerations apply to the bridging group $R_3$. $R_1$ and $R_2$ in the compounds of the formula IIa are preferably identical groups $-SiR_4R_5R_6$.

1,3-Pent-4-enediol which is used is known, and its preparation described by C. Kaneko in Synthesis, page 876 (1974).

Examples of suitable leaving groups X are halide, in particular $Cl^\ominus$, $Br^\ominus$, as well as $CF_3COO^\ominus$, $RSO_3^\ominus$, $SO_4^{2\ominus}$, $PO_4^{3\ominus}$, $CH_3CO_2^\ominus$, $OH^\ominus$, in which R is $C_1$-$C_6$alkyl or $C_1$-$C_6$alkyl which is partially or completely fluorinated, or phenyl or benzyl which are unsubstituted or substituted by $C_1$-$C_4$alkyl, $C_1$-$C_4$alkoxy or halogen (for example F, Cl or Br). The compounds mentioned in process step a2) in which two X are a leaving group are, in particular, aldehydes and ketones which are used for the acetalisation, or ketalisation, of the 1,3-pentenediols used. The compounds $R_1X$, $R_2X$ and $XR_3X$ are generally known and described in the literature. Preferred leaving groups in silylation reagents are $Cl^\ominus$, $Br^\ominus$, $CF_3SO_3^\ominus$ and $CF_3COO^\ominus$.

The reactions in process steps a) and b) can be carried out expediently in the presence of an inert solvent.

Examples of suitable inert solvents are polar or unpolar, preferably aprotic, solvents which can be used on their own or as mixtures of at least two solvents. Examples are: ethers (dibutyl ether, tetrahydrofuran, dioxane, ethylene glycol diethyl ether, ethylene glycol dimethyl ether, diethylene glycol dimethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), carboxylates and lactones (ethyl acetate, methyl propionate, ethyl benzoate, 2-methoxyethyl acetate, γ-butyrolactone, δ-valerolactone, pivalolactone), carboxamides and lactams (N,N-dimethylformamide, N,N-diethylformamide, N,N-dimethylacetamide, tetramethylurea, hexamethylphosphoric triamide, γ-butyrolactam, ε-caprolactam, N-methylpyrrolidone, N-acetylpyrrolidone, n-methylcaprolactam), sulfoxides (dimethyl sulfoxide, sulfones (dimethylsulfone, diethylsulfone, trimethylenesulfone, tetramethylenesulfone), tertiary amines (triethylamine, N-methylpiperidine, N-methylmorpholine), aromatic hydrocarbons, for example benzene or substituted benzenes (chlorobenzene, o-dichlorobenzene, 1,2,4-trichlorobenzene, nitrobenzene, toluene, xylene) and nitriles (acetonitrile, propionitrile, benzonitrile, phenylacetonitrile), as well as aliphatic or cycloaliphatic hydrocarbons (pentane, petroleum ether, hexane, cyclohexane and methylcyclohexane).

Preferred solvents are halogenated aliphatic hydrocarbons, aromatic hydrocarbons, ethers and nitriles, for example methylene chloride, chloroform, benzene, toluene, acetonitrile, diethyl ether, dibutyl ether, tetrahydrofuran and dioxane.

If the compounds $R_1X$ and $R_2X$ are alcohols, or if $XR_3X$ is an aldehyde or a ketone, then the concomitant use of metal salt catalysts or metal complex salt catalysts in a manner known per se is expedient, for example Pd, Pt, Rh and Ru. Examples are tris(triphenylphosphino)rhodium chloride or $Pt(H_2O)_2Cl_2$ or $[(1,1,1-tris(diphenylphosphinomethyl)ethane)Ru(CH_3CN)_3]^{2\ominus}CF_3SO_3^{\ominus})_2$. It can also be expedient to remove the water of reaction which is formed when alcohols, aldehydes or ketones are used, for example by azeotropic distillation or by adding water-binding agents.

The reactions of step a) can be carried out at temperatures from −80° C. up to 250° C., preferably from −20° C. up to the reflux temperature of the solvent used. The choice of the reactants depends essentially on the reactivity of the compounds $R_1X$, $R_2X$ and $XR_3X$.

The compounds of the formulae IIa and IIb can be isolated and purified by customary methods.

The hydroformylation of reaction step b) is advantageously carried out at a temperature from 40° to approximately 200° C. and at a pressure from 1 to 20, preferably 2 to 10, MPa. Suitable solvents have been mentioned above. Preferred solvents are ethers, for example tetrahydrofuran. Suitable catalysts are, for example, free or complexed noble metal salts, for example tris(triphenylphosphino)rhodium chloride. The hydroformylation of ethylenically unsaturated organic compounds is generally known. The mixing ratio of $H_2$ to CO is preferably 1:1.

The compounds of the formula Ia are obtained as a mixture of cis and trans compounds, and this mixture can be separated in order to obtain the trans compound, for example by chromatographic methods. If the compounds of the formula IIb are used, the hydroformylation proceeds surprisingly regioselectively, so that only the desired trans compounds are obtained directly in high yields and purities. The use of the compounds of the formula IIb is therefore preferred. The novel compounds of the formulae Ia and Ib are obtained in the form of a racemate which can be resolved by customary methods. The two enantiomers are also an object of the invention.

The compounds of the formulae Ia and Ib are outstandingly suitable as starting materials for the preparation of carbacyclic nucleosides of the natural and unnatural series or of the enantiomeric mixtures thereof. There is no need for the compounds of the formulae Ia and Ib to be isolated for this purpose, but they can be further processed directly. It is therefore preferred to carry out the hydroformylation in an ether as solvent since the subsequent hydrogenation of the formyl group is expediently carried out in the same solvent.

The invention furthermore relates to compounds of the formulae IIIa and IIIb

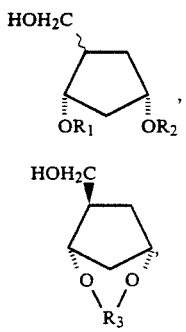

in which $R_1$, $R_2$ and $R_3$ are as defined above, in the form of the racemates thereof and enantiomers thereof, and to the hydroxyl-protected derivatives thereof.

The compounds can be obtained by hydrogenating the compounds of the formulae Ia and Ib. The hydrogenation can be carried out in a manner known per se, catalytically or using metal hydrides, for example LiH, $CaH_2$, $NaBH_4$ or $LiAlH_4$.

Protected means that the hydroxyl group is derivatised with a detachable protective group. Such protective groups and processes for the derivatisation are generally known in sugar chemistry. Examples of such protective groups are: linear or branched $C_1$–$C_8$alkyl, in particular $C_1$–$C_4$alkyl, for example methyl, ethyl, n- and i-propyl, n-, i- and t-butyl; $C_7$–$C_{12}$aralkyl, for example benzyl, methylbenzyl, methoxybenzyl, bromobenzyl; diphenylmethyl, trityl, 4'-monomethoxytrityl, 4',4''-dimethoxytrityl, pixyl; trialkylsilyl having 3 to 20, in particular 3 to 12 C atoms, for example trimethylsilyl, triethylsilyl, tri-n-propylsilyl, i-propyl-dimethylsilyl, t-butyl-dimethylsilyl, t-butyl-diphenylsilyl, n-octyl-dimethylsilyl, (1,1,2,2-tetramethylethyl)-dimethylsilyl; $C_2$–$C_{12}$acyl, in particular $C_2$–$C_8$acyl, for example acetyl, propanoyl, butanoyl, pentanoyl, hexanoyl and benzoyl; $R_{10}$—$SO_2$—, in which $R_{10}$ is $C_1$–$C_{12}$alkyl, in particular $C_1$–$C_6$alkyl, $C_5$- or $C_6$cycloalkyl, phenyl, benzyl, $C_1$–$C_{12}$alkylphenyl, in particular $C_1$–$C_4$alkylphenyl, or $C_1$–$C_{12}$alkylbenzyl, in particular $C_1$–$C_4$alkylbenzyl, or halophenyl or halobenzyl, for example methyl-, ethyl-, propyl-, butyl-, phenyl-, benzyl-, p-bromo-, p-methoxy- and p-methylphenylsulfonyl; $C_1$–$C_{12}$alkoxycarbonyl, preferably $C_1$–$C_8$alkoxycarbonyl, for example methoxy-, ethoxy-, n- or i-propoxy- or n-, i- or t-butoxycarbonyl, phenyloxycarbonyl, benzyloxycarbonyl, methyl- or methoxy- or chlorophenyloxycarbonyl or -benzyloxycarbonyl.

The abovementioned preferred meanings and enumerations also apply to $R_1$, $R_2$ and $R_3$.

The cis and trans isomers of the formula IIIa and the racemates can be resolved by known chromatographic methods. The compounds of the formula IIIb are preferred.

The further reaction of the compounds of the formulae IIIa and IIIb to give carbacyclic nucleosides can be effected for example in the following manner:

The hydroxyl group of the compounds of the formula IIIa and IIIb is protected in a manner known per se, for example using protective groups known from sugar chemistry. Trityl is suitable and may be mentioned as example. The groups $R_2$ and $R_2$, or $R_3$, can be eliminated from the protected compounds in a known manner, for example using aqueous acids or bases or, in the case of Si-containing radicals, using tetrabutylammonium fluoride. The resulting protected diol of the formula IV

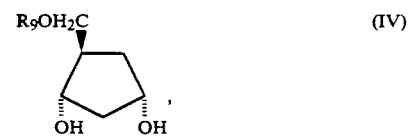

in which $R_9$ is a protective group can be processed in the form of the racemate or converted in high yields into an isomer mixture of the regioisomers of differing absolute configuration of the formulae Va and Vb:

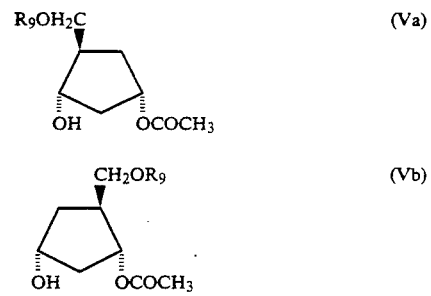

by means of enzymatic catalysed monoacylation using vinyl acetate in the presence of *Pseudomonas fluorescens* lipase or *Chromobakterium viscosum* lipase.

In this enzymatic reaction, $R_9$ is preferably a sterically demanding protective group, for example unsubstituted or $C_1$–$C_4$alkyl or $C_1$–$C_4$alkoxy-substituted diphenylmethyl and, in particular, triphenylmethyl (trityl) as well as t-butyldiphenylsilyl.

The resulting isomer mixture can be completely separated in a simple manner by chromatography on silica gel. The regioisomers which are thus obtained in virtually quantitative yields have high enantiomeric purity (ee at least 98%). Reaction of the compounds of the formulae Va and Vb with bases, for example ammonia, amines or alkali metal bases, in alcoholic solution results in virtually quantitative yields of the enantiomeric diols of the formulae IVa and IVb,

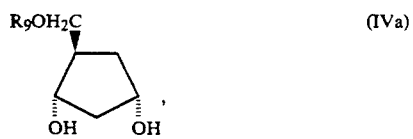

-continued

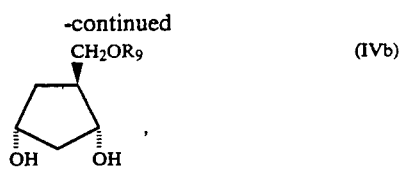

where the compounds of the formula IVa are the (+) enantiomers of the natural series, and, accordingly, the compounds of the formula IVb the (−) enantiomers of the unnatural series.

The racemates of the formula IV and the enantiomers of the formulae IVa and IVb can be reacted with SOCl$_2$ in the presence of tertiary amines to give sulfites which can be oxidised to give the corresponding sulfates of the formulae VI in the form of the racemates thereof or enantiomers thereof, for example by the method described by B. M. Kim and K. B. Sharpless in Tetrahedron Letters 30, page 655 (1989):

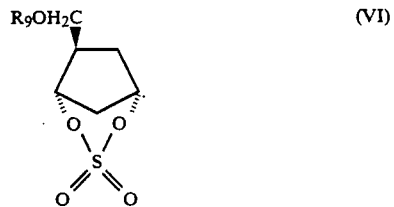

The compounds of the formula VI can be reacted directly with bases, for example adenine or thymine. The reaction is regiospecific, and, in the case of the adenine or thymine, hydrolytic elimination of the sulfate group and elimination of the protective group by known methods give nucleosides of the formula

in which B is 9-adenyl or 1-thymidyl. These pharmaceutical active ingredients and their activity as antiviral active ingredients are described by V. E. Marquezet et al, in Med. Res. Rev., Vol. 6, pages 1–40 (1986). The nucleosides can also be used for the preparation of oligonucleotides which, as in known, also have biological activity, compare E. Uhlmann et al. in Chem. Rev., Vol. 90, No. 4, pages 543–584 (1990).

Despite multi-step synthesis, the total yields of the carbacyclic nucleotides are high. The particular advantage of the synthesis method is the possibility of simultaneously preparing racemates of nucleosides and enantiomers thereof of both the unnatural and the natural series. The process is suitable for being carried out on an industrial scale.

The examples which follow illustrate the invention in greater detail.

A) PREPARATION EXAMPLES

Example 1

Preparation of

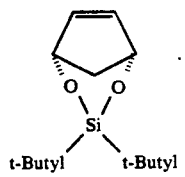

0,91 g (9,1 mmol) of cis-4-cyclopenten-1,3-diol and 20 ml of anhydrous methylene chloride are introduced into a reaction bulb under an argon atmosphere and cooled to 0° C. 3.17 ml (27.3 mmol) of lutidine are added, with stirring, and then, in the course of 10 minutes, 4.42 g (10 mmol) of di-t-butylsilyl ditriflate. The reaction mixture is stirred for 10 minutes at 0° C., the ice-bath is then removed, and stirring is continued for 30 minutes. The solvent is then removed in vacuo, and the oily residue is treated with 20 ml of hexane, with vigorous stirring. The crystalline lutidinium triflate which has formed is filtered off, and the solvent is evaporated from the filtrate. The residue is chromatographed on silica gel using hexane/diethyl ether (20:1), and, after the solvent has been evaporated and the residue dried (room temperature, 30 minutes, 1.3 Pa), 1.4 g (65%) of a colourless oil are obtained. $^1$H NMR (250 MHz, CDCl$_3$): 0.96 and 1.04 (2 s, 2 (C$\underline{H}_3$CSi); 1.81 [dt, J=12.0 and 3.0, $\underline{H}$—C(2)]; 2.49 [d, J=12.0, $\underline{H}$C(2)]. Repetition of the process with five times as much material gives a yield of 80% of theory.

Example 2

Preparation of

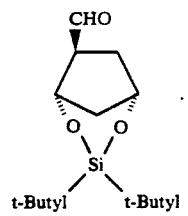

1 g (4.16 mmol) of the compound of Example 1, 15.4 mg (0.4 mol %) of RhCl[P(C$_6$H$_5$)$_3$]$_3$ and 30 ml tetrahydrofuran are introduced into a 50 ml gold-coated autoclave and then heated for 5 hours at 8 MPa and 80° C. under an H$_2$/CO atmosphere. After cooling, the solvent is evaporated in vacuo, and the residue is chromatographed on silica gel (hexane/ethyl acetate 9:1). The solvent is then removed in vacuo, and the residue is dried for one hour at room temperature and 8 Pa. 1.07 g (95%) of the title compound is obtained as a colourless oil. $^1$H NMR (250 MHz, CDCl$_3$): 1.05 and 1,06 (2s,2 (C$\underline{H}_3$CSi); 1.24 [ddd, J=14.0, 3.0 and 3.0, $\underline{H}$—C(2)]; 2.44 [d, J=14.0, $\underline{H}$C(2)]; 9.79 (s, $\underline{H}$CO).

Example 3

Preparation of

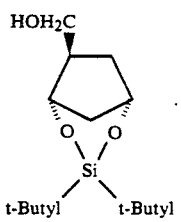

491 mg (1.82 mmol) of the compound of Example 2 are dissolved in 10 ml of tetrahydrofuran/H$_2$O (9:1), and the mixture is cooled to 0° C. 34.5 mg (0.91 mmol) of NaBH$_4$ are then added in one portion, with stirring, and stirring is continued for a further 10 minutes. The solvent is then evaporated, the residue is extracted twice using 30 ml portions of ethyl acetate, and the organic phase is washed with 20 ml of each 2.5-per cent aqueous NaHCO$_3$ and concentrated aqueous sodium chloride solution. The organic phase is then dried using Na$_2$SO$_4$ and filtered, and the filtrate is evaporated to dryness. After the residue has been dried in a high vacuum at room temperature for one hour, 485 mg (98%) of the title compound are obtained as a colourless oil having a small residue content of ethyl acetate. $^1$H NMR (300 MHz, CDCl$_3$): 1.04 and 1.05 (2s, 2 C$\underline{H}_3$CSi); 1.38 (ddd, J=14.5, 5.0 and 5.0) and 1.47 (ddd, J=3.5, 3.5 and 13.5) and 2.30 (ddd, J=3.0, 8.5 and 14.5) and 2.42 (d, J=13.5), [$\underline{H}_2$—C(2) and $\underline{H}_2$C(5)]; 1.59 [s, $\underline{HO}$CH$_2$); 3.36 [dd, J=8.5 and 10.5, H$\underline{O}\underline{H}_2$C(6)].

Example 4

Preparation of

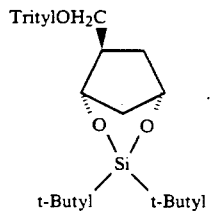

397 mg (1.46 mmol) of the compound of Example 3, 17.8 mg (0.15 mmol) of 2-dimethylaminopyridine and 405 µl (2.91 mmol) of triethylamine are dissolved in 5 ml of CH$_2$Cl$_2$ under an argon atmosphere. 528 mg (1.89 mmol) of trityl chloride are then added in one portion at room temperature while the solution is stirred, and stirring is continued for 18 hours. The solvent is then evaporated in vacuo and the residue is extracted using two 50 ml portions of hexane/ethyl acetate. Hereupon, the solution is washed with in each case 30 ml of aqueous 6-per cent NaHCO$_3$ and concentrated sodium chloride solution, dried using Na$_2$SO$_4$ and filtered, the solvent is evaporated in vacuo, and the residue is dried overnight at room temperature in a high vacuum. 657 mg (88%) of the title compound are obtained. $^1$H NMR (250 MHz, CDCl$_3$): 1.04 and 1.05 (2s, 2 (C$\underline{H}_3$CSi); 1.32-1.50 (m) and 2.22 (ddd, J=14.5, 3.0 and 9.0) and 2.35 (d, J=13.5), [$\underline{H}_2$—C(2) and H$_2$C(5)]; 2.66 [m, HC(4)], 4.43-4.58 [m, $\underline{H}$—C(1.3)]; 7.17-7.47 [m, 15H—C(aromatic)].

Example 5

Preparation of

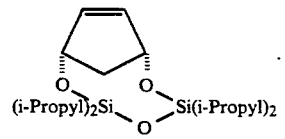

4.05 g (40.5 mmol) of cis-4-cyclopentene-1,3-diol are dissolved in 60 ml of absolute pyridine under argon and added by means of a syringe to 14.18 g (45.0 mmol) of 1,3-dichloro-1,1,3,3-tetraisopropyldisiloxane in the course of 15 minutes at room temperature (RT), during which process the temperature rises slowly to 35° C. The reaction mixture (pyridinium hydrochloride starts to crystallise slowly) is stirred for 16 hours at RT and subsequently evaporated on a rotary evaporator. Two extractions from half-saturated NaHCO$_3$ solution using petroleum spirit, drying of the organic phase over Na$_2$SO$_4$, filtration and concentration give 10.22 g of crude product which is purified by distillation using a bulb tube (130° C., 13 Pa): 8.16 g (75.4%) of colourless oil. $^1$H NMR (250 MHz, CDCl$_3$): 6.08 (s, H—C(4.5)); 4.82 (d, J=8.0, H—C(1.3)); 2.54 (dt, J=15.5, 7.5, H—C(2)); 1.99 (d, J=15.5, H—C(2)); 0.8-1.1 (m, 4 (CH$_3$)$_2$CHSi).

Example 6

Preparation of

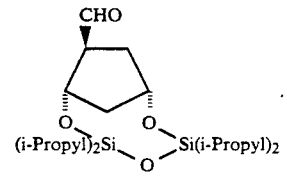

The procedure is analogous to Example 2. 2.00 g of the compound of Example 5 give, after chromatographic purification on SiO$_2$ (hexane/diethyl ether 15:1), 1.93 g (89%) of pure product as a colourless, highly viscous oil. $^1$H NMR (250 MHz, CDCl$_3$): 9.87 (apparent s, CHO); 4.84 (dd, J=7.0, 3.5, H—C(3)); 4.64 (apparent t, J=4.5).

Example 7

Preparation of

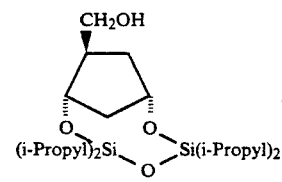

The procedure is analogous to Example 3 except that 1.69 g of the compound of Example 6 are used. 1.70 g (100%) of product are obtained after the extraction as a colourless, highly viscous oil. $^1$H NMR (250 MHz, CDCl$_3$): i.a. 4.57 (apparent t, J=4.5) and 4.39 (dd, J=8.0, 6.0)(H—C(1.3)); 3.73 (J=6.0, 10.5) and 3.64 (J=6.5, 10.5)(ABM system, C$\underline{H}_2$OH).

Example 8

Preparation of

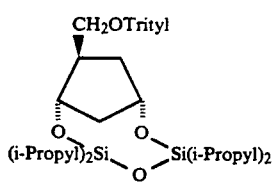

The procedure is analogous to Example 4 except that 1.60 g of compound of Example 7 are used. After purification by column chromatography on silica gel (petroleum spirit/ethyl acetate 30:1), 2.75 g (quantitative yield) of the title compound are obtained as a pale yellowish resin. $^1$H NMR (250 MHz, CDCl$_3$): i.a. 4.52 (apparent t, J=4.0) and 4.30 (dd, J=7.5, 4.0)(H—C(1.3)); 3.15 (J=6.5, 9.0) and 3.03 (J=7.0, 9.0)(ABM system, C$\underline{H}_2$OTr).

B) USE EXAMPLES

Example B1

Preparation of

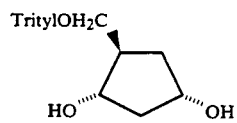

in the form of a racemate.

A solution of 752 mg (2.39 mmol) of tetra-n-butylammonium fluoride trihydrate in 10 ml of tetrahydrofuran is added to 558 mg (1.08 mmol) of the compound of Example 4 and the mixture is stirred for 5 hours at room temperature. The solvent is then evaporated in vacuo, the residue is dissolved in ethyl acetate/hexane (2:1), and the solution is chromatographed on silica gel. The fractions are collected, the solvent is evaporated in vacuo, and the residue is then dried for 18 hours in a high vacuum at room temperature. 409 mg of the title compound are obtained (quantitative yield) as a colourless and resinous substance which recrystallises upon standing. Recrystallisation from ethyl acetate/hexane (1:2) gives a crystalline substance having a melting point of 116°-117° C. $^1$H NMR (250 MHz, CDCl$_3$): 1.48 (ddd, J=5.5, 8.8.and 14.0) and 1.78 (m, 2 main signals) and 1.88-2.08 (m) [$\underline{H}_2$—C(2) and $\underline{H}_2$—C(5)]; 2.51 [$\underline{H}$—C(4)]; 2.03 (d, J=5.0) and 2.58 [d, J=5.0, HO—C(1.3)]; 2.93 [dd, J=8.5 and 8.5, $\underline{H}$—C(6)]; 3.21 [dd, J=5.5 and 9.0, $\underline{H}$—C(6)]; 4.09 and 4.32 [2 m, $\underline{H}$—C(1.3)]; 7.18-7.46 [m, $\underline{H}$—C(aromatic)].

Using 2.75 g of the compound of Example 8, the procedure is followed analogously using 5 mmol equivalents of tetra-n-butylammonium fluoride. After purification by column chromatography, 1.56 g (93%) of a viscous oil are obtained from which 1.23 g (74%) of a colourless crystalline substance is obtained by crystallisation which is identical to the previously prepared substance.

Example B2

Preparation of

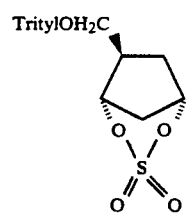

in the form of a racemate.

a) 1.049 g (2.80 mmol) of the compound of Example B1 are dissolved in 20 ml of CH$_2$Cl$_2$ and 1.56 ml (11.4 mmol) of triethylamine under an argon atmosphere. The stirred solution is cooled to 0° C., and 302 μl (4.2 mmol) of SOCl$_2$ are added dropwise in the course of 5 minutes. The colour of the reaction mixture changes from colourless via yellow to brown, and a brown solid precipitates after 10 minutes. The reaction mixture is thereupon extracted twice using 20 ml of ice-cold water and then using 30 ml of ice-cold sodium chloride solution (18% by volume). The organic phase is then dried over MgSO$_4$ and filtered, and the filtrate is evaporated to dryness in vacuo at 15° C. The residue is dissolved twice in in each case 6 ml of CH$_3$CN, re-evaporated to dryness and dried for 10 minutes in a high vacuum. 1.335 g of the title compound are obtained (113%, contains CH$_3$CN and triethylamine as impurities) and used in this form in process b) below.

b) 8.50 g of the compound prepared following a) are dissolved in 160 ml of CH$_3$CN/CCl$_4$ (1:1) and the solution is cooled to 0° C. Then, 120 ml of water, 47 mg (200 μmol) of RuCl$_3$xH$_2$O and 5.71 g (26.7 mmol) of NaIO$_4$ are added in succession. The mixture is stirred vigorously for one hour, 300 ml of diethyl ether are then added, and the aqueous phase is removed. The organic phase is washed three times using 100 ml of ice-cold and concentrated aqueous sodium chloride solution, dried over MgSO$_4$ and filtered, the filtrate is evaporated in vacuo at 15° C., and the residue is then dried in a high vacuum. 5.80 g (99.5%, based on the two process steps) of the title compound are obtained as a colourless and amorphous solid. $^1$H NMR (250 MHz, CDCl$_3$): 1.61 (dt, J=13.5 and 4.0) and 1.77 (dt, J=12.5 and 2.5) and 2.69 (d, J=12.5) and 2.80-2.92 (m, partially overlapping signals) [$\underline{H}_2$—C(2) and $\underline{H}_2$—C(5)]; 3.39 [m, $\underline{H}$—C(4)]; 2.84 (dd, J=8.5 and 7.5,) and 3.29 [dd, J=8.5 and 4.5, $\underline{H}_2$—C(6)]; 5.09 (broad s) and 5.22 [broad s, $\underline{H}$—C(1.3)]; 7.21-7.45 [m, $\underline{H}$—C(aromatic)].

Example B3

Preparation of

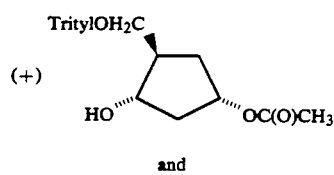

(a)

and

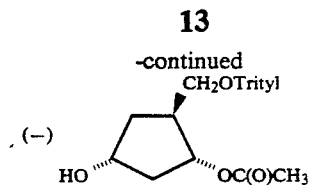

6.22 g (16.6 mmol) of the compound of Example B1 are dissolved in 63 ml of vinyl acetate and treated with 1.24 g of Pseudomonas fluorescens lipase (PFL). The heterogenous reaction mixture is then stirred for 50 hours at room temperature. The mixture is then evaporated in vacuo, the residue is taken up in hexane/ethyl acetate (2:1), and the mixture is chromatographed on silica gel. This gives 250 mg of the diacetate compound, 3.38 g of pure compound (a) and 3.45 g of pure compound (b) as well as 970 mg of unseparated monoacetates, which are rechromatographed. The combined pure compounds (a) and (b) are dissolved three times in $CH_3CN$ and the solutions are evaporated to dryness in vacuo. This gives 3.00 g (43.5%) of compound (a) and 3.15 g (45.5%) of compound (b) as pale yellow oils containing small amounts of $CH_3CN$ as impurities.

$^1$H NMR (250 MHz, $CDCl_3$) of compound (a), (1S,3S,4R)-trans-4-trityloxy-cis-3-hydroxy-1-acetoxy-cyclopentane: 1.54 [m, H—C(5)]; 1.74 [m, $H_2$C(2)]; 1.89 [m, H—C(5)]; 2.05 (s, $H_3$CCOO); 2.40 [m, H—C(2) and H—C(4)]; 2.52 [d, J=4.0, HO—C(3)]; 2.98 [t, J=8.5, H—C(6)]; 3.34 [dd, J=9.0 and 5.0, H—C(6)]; 3.95 [dq, J=3.0 and 7.0, H—C(3)]; 5.07 [m, H(1)]; 7.21–7.45 [m, H—C(aromatic)]. Compound (a) is obtained in an optical purity of ee=98.2% (determined by HPLC, Chiracel ® OD, hexane/i-propanol 9:1, flow rate 1 ml/minute).

$^1$H NMR (250 MHz, $CDCl_3$) of compound (a), (1R,3R,4S)-trans-4-trityloxy-cis-1-hydroxy-3-acetoxy-cyclopentane: 1.61–178 [m, H—C(2,5) and HO—C(1)]; 1.95 [m, H—C(5)]; 2.03 [s, $H_3$—CCOO]; 2.30 [ddd, J=14.5 and 7.5 and 5.5, H—C(2)]; 2.60 [m, H—C(4)]; 3.12 [ABM system, $H_2$—C(6)]; 4.34 [m, H—C(1)]; 5.05 [m, H—C(3)]; 7.18–7.45 [m, H—C(aromatic)]. Compound (b) is obtained in an optical purity of ee 98.6%.

Example B4

Preparation of

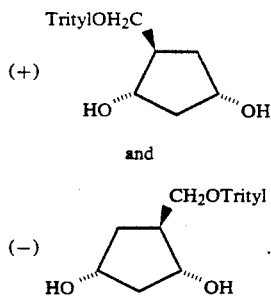

100 g (240 mmol) of the monoacetates of Example B3 are dissolved in 600 ml of methanol under argon, and 188.5 g (4.8 mol) of ethylenediamine are added, during which process the temperature rises to 50° C. The reaction mixture is stirred at this temperature for 15 hours. The solvent is then evaporated under a high vacuum, and the residue is taken up three times in acetonitrile and re-evaporated. The oil obtained is dissolved in 500 ml of ethyl acetate, 300 ml of water are added, and aqueous citric acid solution (10%) is added, with stirring. After an addition of a further 500 ml of ethyl acetate, the organic phase is separated off and the aqueous phase is extracted twice using 150 ml portions of ethyl acetate. The combined organic phases are dried over $NaHCO_3$ and then evaporated. The residue is taken up twice in acetonitrile and evaporated and then recrystallised from cyclohexane (1 week, 8°–10° C.). After drying, in each case 85.2 g (95%) of the title compounds are obtained as colourless crystals. The $^1$H NMR spectra are identical to the racemate of Example B1.

Compound (a): melting point 105°–106° C.; $[\alpha]^{25}$= +24.1 (589, c=1.0, $CH_3OH$), +73.7 (365 nm).

Compound (b): melting point 105°–106° C.; $[\alpha]^{25}$= −25.8 (589, c=1.0, $CH_3OH$), −75.2 (365 nm).

Example B5

Preparation of

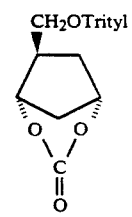

in the form of a racemate 200 mg (534 μmol) of the compound of Example B1 are suspended in toluene, a small amount of molecular sieve (3 Å) is added, and the mixture is stirred for approximately 5 minutes under argon. 5 minutes after 95.3 mg (588 μmol) of carbonyldiimidazole have been added, the reaction mixture turns clear. After the reaction mixture has been stirred for 36 hours at 90° C. and for 45 days at room temperature, it is evaporated on a rotary evaporator and purified on silica gel (ethyl acetate/hexane 1:2). The pure product fractions are combined and concentrated, and this is then taken up in $CH_3CN$ and reconcentrated. 53 mg (25%) of pure product are obtained.

$^1$H NMR (250 MHz, $CDCl_3$): i.a. 4.84 (m) and 4.78 (m)(H—C(1.3)); 3.22 (quartet-like m, H—C(4)); 2.84 (m, $CH_2$OTr).

Example B6

Preparation of
(±)-cis-4-hydroxymethyl-1-(9-adenyl)-trans-3-hydroxy-cyclopentane

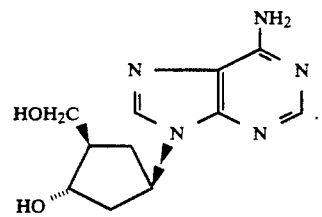

a) 297 mg (2.20 mmol) of adenine are suspended in 10 ml of $CH_3CN$ under an argon atmosphere, and 337 mg (2.21 mmol) of 1,8-diazabicyclo[5,4,0]undec-7-ene are then added. The mixture is stirred for 15 minutes at room temperature and subsequently treated with 0.50 g (1.15 mmol) of the racemate of Example B2. The reaction mixture is then stirred for a further 15 hours at room temperature. After the solvent has been evaporated in vacuo, the residue is taken up in CH$_2$Cl$_2$/methanol/triethylamine (30:3:1) and the mixture is chromatographed on silica gel. The combined fractions are evaporated to dryness, and the residue is dissolved twice in 20 ml portions of CH$_3$CN and re-evaporated to dryness. The residue is then dissolved in 30 ml of water and treated with triethylamine. The precipitate is filtered off and dried. This gives 590 mg (76%) of the tetraethylammonium salt of ($\pm$)-cis-4-trityloxymethyl-1-(9-adenyl)-trans-3-sulfato-cyclopentane as a colourless powder. $^1$H NMR (250 MHz, CD$_3$OD): 1.31 [t, J=7.0, (CH$_3$CH$_2$)$_3$NH$^+$]; 3.20 [q, J=7.0, (CH$_3$CH$_2$)$_3$NH$^+$]; 1.64–2.66 [m, H$_2$—C(2',5') and H—C(4')]; 3.15–3.40 [m, H$_2$—C(6')]; 5.02–5.17 [m,H—C(1',3')]; 7.18–7.51 [m, H—C(trityl)]; 8.15 and 8.16 [2s, H—C(adenine)].

b) 200 mg of the compound prepared in accordance with a) are dissolved in each case in 10 ml of 2N HCl and ethanol, and the solution is heated for 24 hours at 80°–85° C. The solvent is then evaporated in vacuo, and the residue is taken up twice in 20 ml portions of CH$_3$CN and evaporated. The crude product obtained is taken up in methanol/ethyl acetate (1:1) and chromatographed on silica gel. After the solvent has been evaporated, the residue is recrystallised using the same solvent. This gives 80.1 mg (94%) of ($\pm$)-cis-4-hydroxymethyl-1-(9-adenyl)-trans-3-hydroxy-cyclopentane hydrochloride in the form of colourless crystals.

$^{13}$C NMR (63 MHz, CD$_3$OD): 35.1 (C(2')), 41.7 (C(6')), 50.7 (C(4')), 55.9 (C(1')), 64.2 (C(5')), 73.7 C(3')), 120.3, 150.3 and 151.7 (C(4',5',6')), 144.,3 and 144.,7 (HC(2,8)).

c) 400 mg (1.40 mmol) of the compound obtained in accordance with b) are dissolved in methanol and filtered through a column containing 10 g of amberlite IRA-93 (OH form). The collected fractions are evaporated in vacuo, and the residue is taken up twice in CH$_3$CN and evaporated. The residue is dissolved in methanol, the solution is heated to reflux, and methyl acetate is added until the mixture turns slightly cloudy. The mixture is then allowed to crystallise overnight at 4° C., and the crystals are filtered off and dried in a high vacuum. This gives 320 mg (92%) of the title compound in the form of colourless crystals having a melting point of 183° to 185° C. $^1$H NMR (250 MHz, CD$_3$OD): 1.94 (dt, J=12.5, 10.0) and 2.14–2.66 (m)(H$_2$—C(2',6') and H—C(4')); 3.72 (ABM system, H$_2$—C(5')); 4.32 (m, H—C(3')); 5.24 (quint.-like m, H—C(1')); 8.41 (s) and 8.48 (s)(H—C(2.8)).

Example B7

Preparation of (1R,3S,4R)-cis-4-hydroxymethyl-trans-3-hydroxy-1-(9'-adenyl)-cyclopentane hydrochloride Compound (a) of Example B4 is converted into the cyclic sulfate as described in Example B2, and 11.50 g (26.3 mmol) are reacted with 3.76 g (27.8 mmol) of adenine as described in Example B6. This gives 14.25 g (80.4%) of the crystalline title compound.

$^1$H NMR (250 MHz, CD$_3$OD): 1.94 (dt, J=12.5, 10.0) and 2.14–2.66 (m)(H$_2$—C(2',6') and H—C(4')); 3.72 (ABM system, H$_2$—C(5')); 4.32 (m, H—C(3')); 5.24 (quintet-like m, H—C(1')); 8.41 (s) and 8.48 (s)(H—C(2,8)).

Example B8

Preparation of (1S,3R,4S)-cis-4-hydroxymethyl-trans-3-hydroxy-1-(9'-adenyl)-cyclopentane The procedure is as described in Example B7, except that compound (b) of Example B4 is used. This gives 76.9% of the title compound in the form of colourless crystals, melting point 185°–186° C., $[\alpha]^{25} = -10.2$ (589, c=0.5, H$_2$O).

What is claimed is:

1. A compound of the formula Ib

in which R$_3$ is a bridging member which, together with the radical —OCH—CH$_2$—CHO— to which it is bonded, forms a 6- to 8-membered ring, said bridging member being selected from the group consisting of alkylidene having 1 to 20 C atoms, cycloalkylidene having 5 to 8 ring carbon atoms, a radical of the formula R$_7$R$_8$Si= and a radical of the formula —SiR$_7$R$_8$—O—R$_7$R$_8$Si—, in which R$_7$ and R$_8$, independently of one another, are linear or branched C$_1$–C$_{12}$alkyl, phenyl, benzyl, or phenyl or benzyl, which are substituted by C$_1$–C$_4$alkyl or C$_1$–C$_4$alkoxy.

2. A compound of claim 1 wherein R$_3$ is C$_1$–C$_6$alkylidene or benzylidene.

3. A compound of claim 1 wherein R$_3$ is selected from the group consisting of methylene, phenylmethylene, diphenylmethylene, phenyl-methyl-methylene, ethylidene, 1,1- or 2,2-propylidene, 1,1- or 2,2-butylidene, 1,1-, 2,2- or 3,3-pentylidene, 3,3-dimethyl-2,2-butylidene, 1,1-, 2,2-and 3,3-hexylidene, octylidene, dodecylidene, cyclopentylidene and cyclohexylidene.

4. A compound of claim 1 wherein R$_3$ is selected from the group consisting of R$_7$R$_8$Si= and —SiR$_7$R$_8$—O—R$_7$R$_8$Si—.

5. A compound of claim 4 wherein R$_3$ is —SiR$_7$R$_8$—O—R$_7$R$_8$Si—.

6. A compound of claim 4 wherein R$_3$ is a radical selected from the group consisting of dimethylsilylidene, diethylsilylidene, di-n-propylsilylidene, di-i-propylsilylidene, di-n-butylsilylidene, di-i-butylsilylidene, di-t-butylsilylidene, diphenylsilylidene, phenylmethylsilylidene, i-propylmethylsilylidene, t- or n-butylmethylsilylidene, n-hexylmethylsilylidene, n-octylmethylsilylidene, n-dodecylmethylsilylidene and (1,1,2,2-tetramethylethyl)methylsilylidene and tetramethyl-, tetraethyl-, tetra-n-propyl-, tetra-i-propyl-, tetra-n-butyl-, tetra-i-butyl- or tetra-t-butyl-, 1,3-dimethyl-1,3-di-t-butyl-2-oxa-1,3-disila-prop-1,3-diyl.

7. A compound according to claim 1, wherein R$_3$ as alkylidene contains 1 to 14 C atoms.

8. A compound according to claim 4, wherein R$_7$ and R$_8$ independently of one another are C$_1$–C$_{12}$alkyl or phenyl.

9. A compound according to claim 1, wherein $R_3$ is a radical of the formula $R_7R_8Si=$ or $-SiR_7R_8-O-R_7R_8Si-$.

10. A compound according to claim 9, wherein $R_7$ and $R_8$ are identical radicals and are $C_1-C_6$alkyl.

11. A compound of the formula IIb

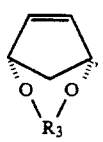
(IIb)

in which $R_3$ is as defined in claim 1.

12. A compound according to claim 11, wherein $R_3$ is a radical of the formulae $R_7R_8Si=$ or $-SiR_7R_8-O-R_7R_8Si-$ in which $R_7$ and $R_8$ independently of one another are as defined in claim 1.

13. A compound of claim 1 having the formula

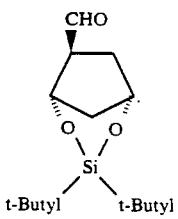

14. A compound of the formula IIIb

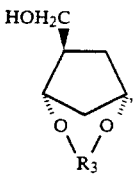
(IIIb)

in which $R_3$ is a bridging member which, together with the radical $-OCH-CH_2-CHO-$ to which it is bonded, forms a 6- to 8-membered ring, said bridging member being selected from the group consisting of alkylidene having 1 to 20 C atoms, cycloalkylidene having 5 to 8 ring carbon atoms, a radical of the formula $R_7R_8Si=$ and a radical of the formula $-SiR_7R_8-O-R_7R_8Si-$, in which $R_7$ and $R_8$, independently of one another, are linear or branched $C_1-C_{12}$alkyl, phenyl, benzyl, or phenyl or benzyl, which are substituted by $C_1-C_4$alkyl or $C_1-C_4$alkoxy; in the form of a racemate thereof or enantiomer thereof, as well as a hydroxyl-protected derivative thereof.

15. A compound of claim 14 wherein $R_3$ is selected from the group consisting of $R_7R_8Si=$ and $-SiR_7R_8-O-R_7R_8Si-$.

16. A compound according to claim 14, wherein the protected derivative comprises a detachable protective group from the group consisting of linear or branched $C_1-C_8$alkyl, $C_7-C_{12}$aralkyl, diphenylmethyl, trityl, trialkylsilyl having 3 to 20 C atoms, $C_2-C_{12}$acyl or $R_{10}-SO_2-$, in which $R_3$ is $C_1-C_{12}$alkyl, $C_5-$ or $C_6$cycloalkyl, phenyl, benzyl, $C_1-C_{12}$alkylphenyl or $C_1-C_{12}$alkylbenzyl, or halophenyl or halobenzyl or $C_1-C_{12}$alkoxycarbonyl.

17. A compound of claim 15 wherein $R_3$ is $-SiR_7R_8-O-R_7R_8Si-$.

18. A compound of claim 15 wherein $R_3$ is a radical selected from the group consisting of dimethylsilylidene, diethylsilylidene, di-n-propylsilylidene, di-i-propylsilylidene, di-n-butylsilylidene, di-i-butylsilylidene, di-t-butylsilylidene, diphenylsilylidene, phenylmethylsilylidene, i-propylmethylsilylidene, t- or n-butylmethylsilylidene, n-hexylmethylsilylidene, n-octylmethylsilylidene, n-dodecylmethylsilylidene and (1,1,2,2-tetramethylethyl)methylsilylidene and tetramethyl-, tetraethyl-, tetra-n-propyl-, tetra-i-propyl, tetra-n-butyl-, tetra-i-butyl- or tetra-t-butyl-, 1,3-dimethyl-1,3-di-t-butyl-2-oxa-1,3-disila-prop-1,3-diyl.

* * * * *